United States Patent [19]

Lindberg

[11] Patent Number: 4,669,450

[45] Date of Patent: Jun. 2, 1987

[54] HEEL CORD STRETCHING APPLIANCE AND METHOD

[75] Inventor: Warren N. Lindberg, Seattle, Wash.

[73] Assignees: Bill Kelly; Diana D. Cardenas, both of Seattle, Wash.; part interest to each

[21] Appl. No.: 723,383

[22] Filed: Apr. 15, 1985

[51] Int. Cl.[4] .......................... A61H 1/02; A61F 1/05

[52] U.S. Cl. ............................... 128/25 B; 128/80 R; 272/96

[58] Field of Search ................. 128/25 R, 25 B, 80 R, 128/80 A, 80 B, 80 C, 80 DB, 80 E, 80 F, 80 G, 84 R, 87 R, 87 C, 88, 75; 272/116, 126, 117

[56] References Cited

U.S. PATENT DOCUMENTS

| | | | |
|---|---|---|---|
| 764,687 | 7/1904 | Shultz | 128/75 |
| 1,257,297 | 2/1918 | Brown | 128/88 |
| 1,399,606 | 12/1921 | Ferragamo . | |
| 2,542,074 | 2/1951 | Bierman | 272/117 X |
| 3,618,598 | 11/1971 | Davis | 128/85 |
| 3,804,085 | 4/1974 | Eshuis et al. | 128/85 |
| 3,942,521 | 3/1976 | Klippel | 128/85 |
| 4,003,374 | 1/1977 | Mizrachy | 128/25 B |
| 4,050,455 | 9/1977 | Smith | 128/80 F |
| 4,474,176 | 10/1984 | Farris et al. | 128/25 B |

FOREIGN PATENT DOCUMENTS

| | | | |
|---|---|---|---|
| 847795 | 8/1952 | Fed. Rep. of Germany | 128/87 R |
| 2375856 | 9/1978 | France | 128/80 R |
| 72225 | 12/1945 | Norway | 128/87 R |

*Primary Examiner*—Richard J. Apley
*Assistant Examiner*—J. Welsh
*Attorney, Agent, or Firm*—Ward Brown; Robert W. Beach

[57] ABSTRACT

An elongated rigid legboard is secured to the back of the leg of a patient suffering from a contracture of the heel cord and/or its associated muscles. Straps connected to the legboard hold the knee joint in fully extended position. A footboard pivotally mounted on the legboard is swung upward to engage against the underside of the patient's foot and apply a force tending to swing the foot upward, which thereby applies stretching force to the heel cord to treat the contracture. A ratchet permits upward swinging movement of the footboard relative to the legboard as the force is applied but prevents downward swinging movement of the footboard relative to the legboard when the force is removed so that static tension force continues to be applied to the heel cord.

5 Claims, 4 Drawing Figures

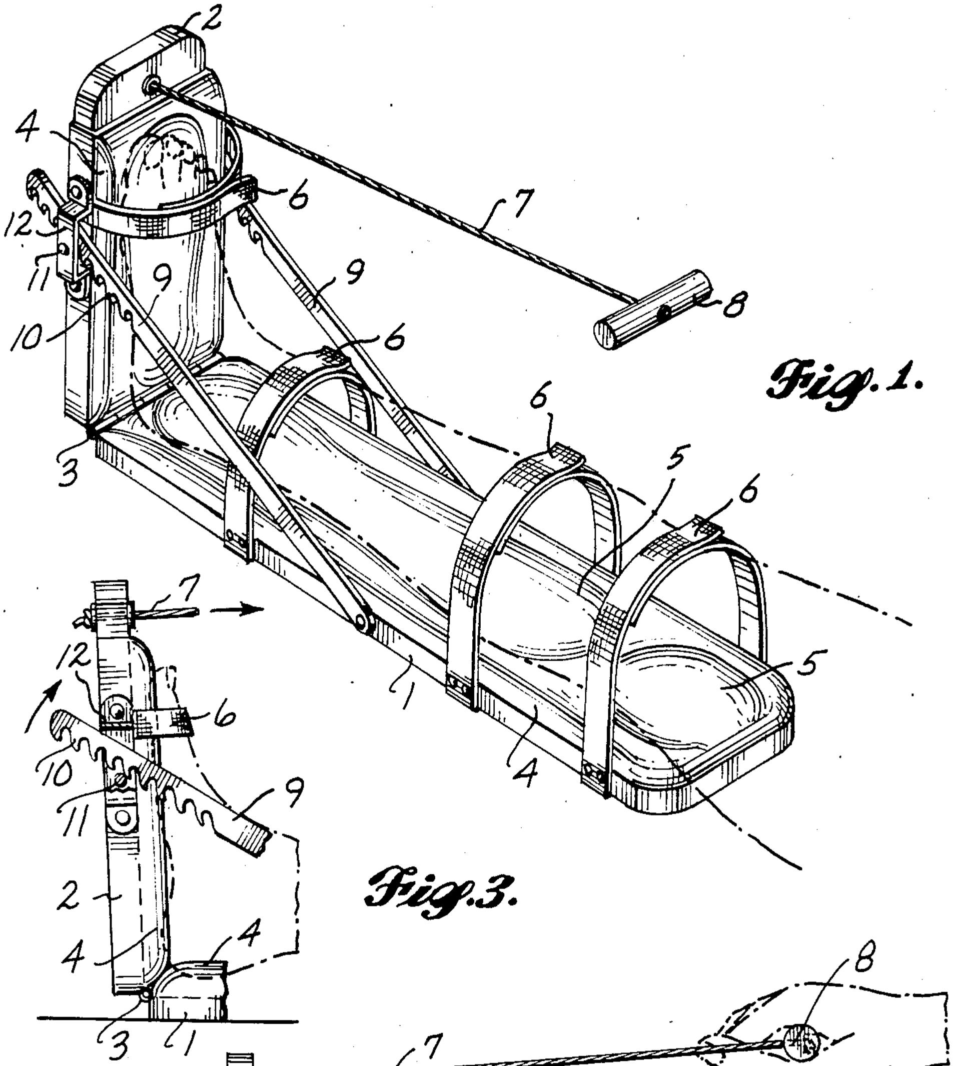
Fig. 1.
Fig. 3.
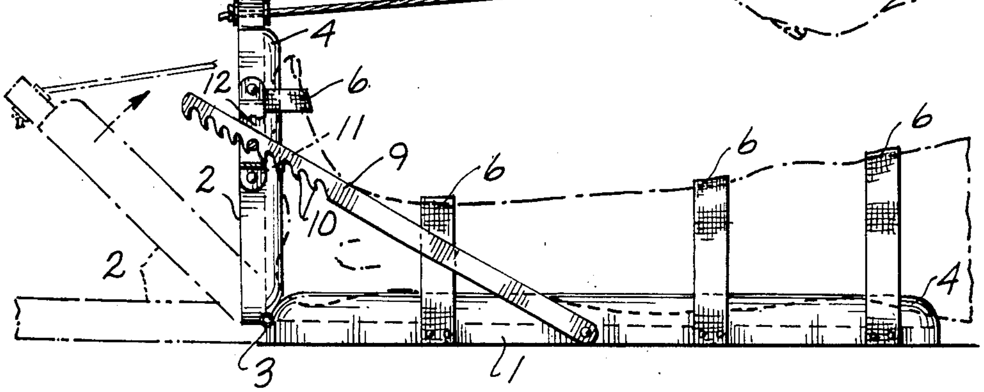
Fig. 2.

HEEL CORD STRETCHING APPLIANCE AND METHOD

BACKGROUND OF THE INVENTION

1. Field of the Invention

The present invention relates to an appliance used in the general field of kinesitherapy for applying static tension force to the gastrocnemius-calcaneus tendon and its associated muscles to treat a contracture and thereby increase the range of motion of the ankle joint. Such tendon is commonly referred to as the heel cord.

2. Problem

In the absence of regular stretching activity of the heel cord, a contracture may occur, namely, tightening of the heel cord and its associated muscles. Such a contracture results in a downward inclination of the foot resistive to normal upward motion. For example, the abnormal downward inclination of the foot can result from a patient being bedridden or chairbound or following complete or partial immobilization of the ankle joint for treatment of an orthopedic or soft tissue injury, such as after injury to the heel cord itself or nearby bones.

PRIOR ART

Conventional treatment of the contracture is by applying stretching force to the heel cord, often under the supervision of a therapist or physician, with or without warming of the heel cord by ultrasound. The stretching force is applied by locking the knee joint to maintain the upper and lower leg aligned while applying a strong force tending to swing the foot from the downward-inclined position to a more perpendicular position. Depending on the severity of the contracture and the mobility of the patient this procedure can be much more complicated than it at first appears. For a bedridden patient it is difficult for a therapist to hold the knee joint fully extended and at the same time apply the desired strong force to the foot. Consequently, it is sometimes deemed necessary to strap the affected patient to a tiltable table with the underside of the foot engaged against the footboard of the table. The table is swung to vertical position so that, with the knee joint locked, the full weight of the patient is applied to the underside of the foot tending to swing the foot upward.

SUMMARY OF THE INVENTION

It is an object of the present invention to provide an appliance for treating contracture of the heel cord and its associated muscles by applying tension force to the heel cord.

It also is an object to provide such an appliance usable to apply static tension force to the heel cord for an extended period.

An additional object is to provide such an appliance of simple design and inexpensive to manufacture.

A further object is to provide such an appliance usable by the patient with little or no supervision or assistance.

In the preferred embodiment of the present invention the foregoing objects are accomplished by providing a rigid legboard with straps for securing the legboard to the back of the patient's leg to lock the knee joint, a rigid footboard hinged to the legboard and having a strap for securing the footboard to the underside of the foot, a force-transmitting member that can be operated by the patient to manipulate the footboard so as to apply stretching force to the heel cord, and mechanism for locking the footboard in a desired angular relationship relative to the legboard to maintain the application of the stretching force for a desired period.

BRIEF DESCRIPTION OF THE DRAWINGS

FIG. 1 is a somewhat diagrammatic top perspective of a heel cord stretcher in accordance with the present invention;

FIG. 2 is a somewhat diagrammatic side elevation thereof;

FIG. 3 is a somewhat diagrammatic, fragmentary, side elevation of the bottom end portion thereof.

DETAILED DESCRIPTION

Figure 4:
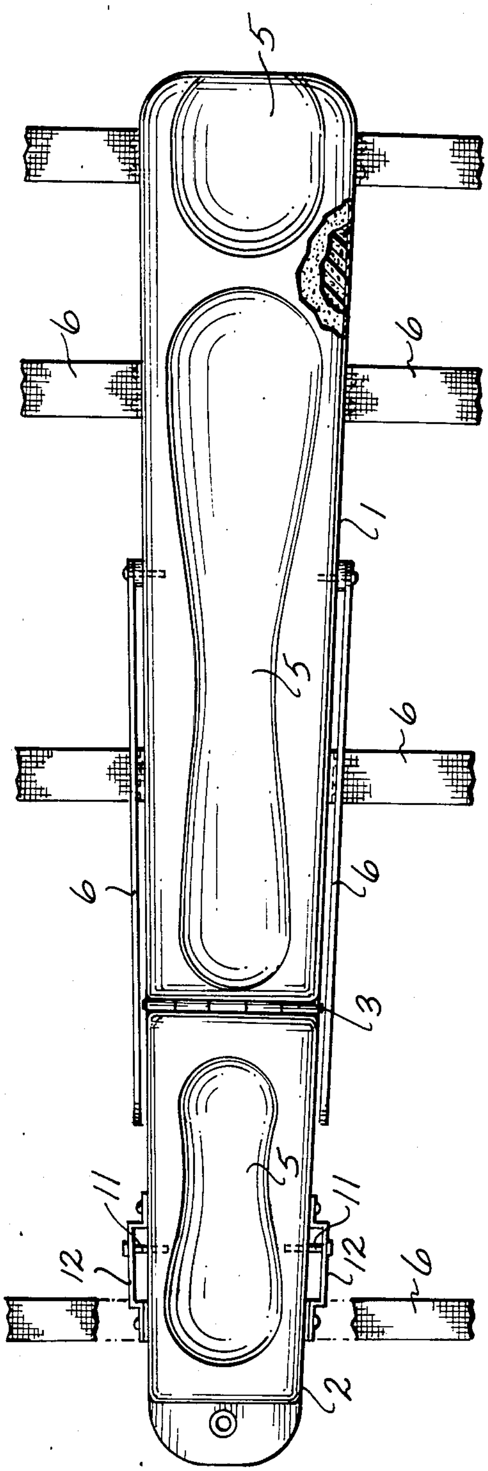
FIG. 4 is a top plan thereof with parts broken away.

As shown in the drawings, the preferred form of a heel cord stretcher in accordance with the present invention includes an elongated rigid legboard 1 of a length sufficient to extend from the heel of a patient to above the knee. Preferably, the width of the legboard is only slightly greater than the width of the leg. A rigid footboard 2 is pivotally connected to one end of the legboard such as by a piano hinge 3. The length of the footboard is substantially greater than the length of the patient's foot and the width of the footboard is preferably at least slightly greater than the width of the patient's foot.

The upper surfaces of the legboard and footboard can have respective layers of resilient padding 4 with depressions 5 approximately contouring the padding to the shape of the back of the leg and the underside of the foot.

Flexible straps 6 are provided to secure the legboard and footboard to the patient as indicated in FIG. 1. Each strap includes a pair of aligned sections having their outer end portions anchored, respectively, to the opposite sides of the legboard or footboard and their inner free end portions overlapping above the patient's leg or foot. The overlapping free end portions of the strap sections can be detachably secured together by an appropriate hook and pile fastening material.

Preferably at least two straps are provided for the legboard, such two straps being disposed closely adjacent to and at opposite ends of the patient's knee joint to lock the knee joint in fully extended position. In the preferred embodiment, a third legboard strap is located slightly above the ankle to assure that the heel is held against the bottom end portion of the legboard. A single strap can be provided on the footboard, positioned in the area of the ball of the foot to hold the underside of the foot against the footboard, but the footboard straps is not as important as the legboard strap.

One end of an elongated force-transmitting member in the form of a rope or cord 7 is connected to the swinging end portion of the footboard 2. For maximum leverage, preferably such member is connected to the footboard at a location centered between the opposite sides of the footboard a substantial distance above the patient's foot. The free end portion of the force-transmitting member has a handle 8.

Ratchet bars 9 have corresponding end portions pivoted, respectively, to the opposite sides of the legboard 1 at about its longitudinal center, that is, approximately in the area of the lower calf of the patient. The swinging end portions of the ratchet bars have downward-extending, longitudinally spaced teeth 10 forming grooves or slots between them which, in the position shown in FIGS. 1 and 2, receive ratchet pins 11 projecting outward from the opposite sides of the footboard 2. The ratchet pins are located approximately midway between the opposite ends of the footboard. U-shaped brackets 12 carried by the footboard have webs extending over the swinging ends of the ratchet bars 9 to maintain the teeth of such bars in alignment with the ratchet pins 11.

In use, the patient can quickly, easily and firmly secure the footboard 2 to the underside of the foot and the legboard 1 to the back of his or her leg by use of the straps 6. As the footboard 2 is swung upward by the patient from a position in substantial alignment or substantially coplanar with legboard 1, the swinging ends of the ratchet bars 9 are fitted in the brackets 12 and above the ratchet pins 11. With the foot engaged with the footboard 2 and the leg secured on the legboard 1 in straight or unbent condition, pulling force is applied to the cord 7 grasping the handle 8 to exert an upward swinging force on footboard 2. With reference to FIG. 3, the teeth 10 of the ratchet bars are inclined slightly toward the ratchet bar pivots so that the bars are automatically raised as the ratchet pins 11 slide under each tooth. When the pins are registered with slots between teeth, the bars fall downward without requiring the patient to release his grasp on the handle and manipulate the ratchet, and act as adjustable length, inclined braces or ties connecting the two boards and preventing retrograde downward swinging of the footboard relative to the legboard. With the footboard perpendicular to the legboard as shown in FIG. 2, the ratchet or brace bars 9 are at a substantial acute angle to the legboard, preferably in the range of 20 degrees to 45 degrees, for a reliable, strong brace connection.

A surprising amount of tension can be applied to the heel cord by the patient exerting a strong pull on the handle 8. Such tension continues to be applied for a desired period when the handle is released. The tension can be increased gradually periodically by the patient pulling on handle 8 at successive intervals to swing the footboard farther upward by increments represented by a notch or two of the ratchets without the heel cord tension being released between such incremental adjustments because it is not necessary for the patient to release his grip on the handle in order to adjust the ratchet manually or to manipulate any locking or holding mechanism to secure the footboard in the newly adjusted position relative to the legboard. At the end of the treating period, the patient can quickly and easily remove the appliance by unfastening the straps. The ratchet bars can be swung up to disconnect them from the ratchet pins and allow the footboard to be swung first downward to remove the bars from the footboard brackets, then all the way upward into engagement with the legboard for compact storage.

I claim:

1. A therapeutic heel cord stretching appliance for a patient comprising an elongated legboard of substantially rigid material, legboard securing means for firmly securing said legboard to the patient's leg in substantially straight condition, an elongated footboard pivotally connected to one end portion of said legboard and engageable with the underside of the patient's foot, an elongated force-transmitting member connected to the swinging end portion of said footboard and of a length to enable the patient to grasp and pull on said force-transmitting member when his leg is thus secured in straight condition, and locking means connected between said legboard and said footboard enabling swinging of said footboard relative to said legboard in one direction to progressively advanced positions to decrease the included angle between said boards so as to apply inceased stretching force to the heel cord and for automatically preventing in each progressively advanced position of said footboard appreciable inadvertent retrograde swinging movement of said footboard relative to said legboard in the opposite direction to increase the included angle between said boards and decrease the stretching force applied to the heel cord without requiring the patient to release his grasp on said force-transmitting member and manipulate said locking means.

2. A therapeutic heel cord stretching appliance for a patient comprising an elongated legboard of substantially rigid material, legboard securing means for firmly securing said legboard to the patient's leg in substantially straight condition, and elongated footboard pivotally connected to one end portion of said legboard at a location remote from its swinging end and engageable with the underside of the patient's foot, a cord connected to the swinging end portion of said footboard of a length to enable the patient to grasp and pull on said cord when his leg is thus secured, and ratchet means connected between said legboard and said footboard enabling incremental swinging of said footboard relative to said legboard in one direction to progressively advanced positions tending to move the patient's foot upward to apply increasing stretching force to the heel cord and for automatically preventing in each progressively advanced position of said footboard appreciable inadvertent retrograde downward swinging movement of said footboard relative to said legboard without requiring the patient to release his grasp on said cord and manipulate said ratchet means.

3. The appliance defined in claim 2, in which the mechanical ratchet means includes an elongated ratchet bar having one end portion pivotally connected to one of the boards intermediate its ends, and a ratchet pin projecting from the other board intermediate its ends, said ratchet bar having inclined slots for receiving said pin.

4. The method of applying therapeutic static stretching force to the heel cord of a patient suffering from a contracture which comprises securing an elongated substantially rigid leg-engaging member extending longitudinally of the leg across the patient's knee joint so as to maintain the knee joint in substantially unbent position, engaging the underside of the foot against a footboard pivotally connected to the leg-engaging member, applying force exerted manually by the patient to the footboard in a direction tending to swing the foot incrementally progressively upward so as to apply stretching force to the heel cord, and automatically mechanically securing the footboard substantially in each progressively upwardly swung position relative to the leg-engaging member by a ratchet connected between the legboard and the footboard without requiring the patient to discontinue application of manual force to the footboard in order to manipulate the ratchet for securing the footboard in such progressively upwardly swung positions for maintaining the application of stretching force to the heel cord.

5. The method of applying therapeutic static stretching force to the heel cord of a patient suffering from a contracture which comprises securing an elongated substantially rigid leg-engaging member extending longitudinally of the leg across the patient's knee joint so as to maintain the knee joint in substantially unbent position, engaging the underside of the foot against a footboard pivotally connected to the leg-engaging member, applying force exerted manually by the patient to the footboard in a direction tending to swing the foot upward so as to apply stretching force to the heel cord, and automatically mechanically securing the footboard substantially in such upwardly swung position relative to the leg-engaging member without requiring the patient to discontinue application of manual force to the footboard in order to secure the footboard in such upwardly swung position for maintaining the application of stretching force to the heel cord.

* * * * *

UNITED STATES PATENT AND TRADEMARK OFFICE
CERTIFICATE OF CORRECTION

PATENT NO. : 4,669,450

DATED : June 2, 1987

INVENTOR(S) : Lindberg, Warren N.

It is certified that error appears in the above-identified patent and that said Letters Patent are hereby corrected as shown below:

Title page, item [21]: the correct application number is --723,393--.

Claim 1, column 4, line 5: change "inceased" to --increased--.

Signed and Sealed this

Third Day of November, 1987

*Attest:*

DONALD J. QUIGG

*Attesting Officer*

*Commissioner of Patents and Trademarks*